(12) United States Patent
Indukuri et al.

(10) Patent No.: US 8,367,834 B2
(45) Date of Patent: *Feb. 5, 2013

(54) PROCESS FOR PREPARING MONTELUKAST AND SALTS THEREOF

(75) Inventors: Venkata Sunil Kumar Indukuri, Hyderabad (IN); Srinivas Simhadri, Hyderabad (IN); Satyanarayana Chava, Hyderabad (IN)

(73) Assignee: Laurus Labs Private Limited, Hyderabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/474,135

(22) Filed: May 17, 2012

(65) Prior Publication Data

US 2012/0232276 A1    Sep. 13, 2012

Related U.S. Application Data

(63) Continuation of application No. 12/673,916, filed as application No. PCT/IN2009/000299 on May 25, 2009, now Pat. No. 8,207,343.

(30) Foreign Application Priority Data

May 26, 2008    (IN) .......................... 1284/CHE/2008

(51) Int. Cl.
    *C07D 215/18*    (2006.01)

(52) U.S. Cl. ....................................................... 546/180
(58) Field of Classification Search ................... 546/180
    See application file for complete search history.

(56) References Cited

U.S. PATENT DOCUMENTS

| 5,523,477 A | 6/1996 | King et al. |
| 5,614,632 A | 3/1997 | Bhupathy et al. |
| 2005/0107612 A1 | 5/2005 | Reguri et al. |
| 2005/0234241 A1 | 10/2005 | Sundaram et al. |
| 2005/0256156 A1 | 11/2005 | Shapiro et al. |

FOREIGN PATENT DOCUMENTS

| EP | 0480717 A1 | 4/1992 |
| WO | 2004108679 A1 | 12/2004 |
| WO | 2005000807 A2 | 1/2005 |
| WO | 2005105749 A2 | 11/2005 |
| WO | 2006008751 A2 | 1/2006 |
| WO | 2006021974 A1 | 3/2006 |

*Primary Examiner* — Taofiq A Solola
(74) *Attorney, Agent, or Firm* — Blank Rome LLP

(57) ABSTRACT

A method for the preparation of montelukast and salts thereof has been described. The method comprises of following steps: (a) (S)-1-(3-((E)-2-(7-chloroquinolin-2-yl)vinyl)phenyl)-3-(2-isopropenylphenyl]propyl methane sulphonate (styrene mesylate salt) (b) coupling with 1-(mercaptomethyl) cyclopropane acetic acid followed by salification with an amine gives styrene amine salt (c) Converting styrene amine salt to Montelukast amine salt (d) Converting Montelukast amine salt to Montelukast free acid and or its required alkali/alkaline salt.

20 Claims, No Drawings

PROCESS FOR PREPARING MONTELUKAST AND SALTS THEREOF

CROSS-REFERENCE TO RELATED APPLICATIONS

The present application is a continuation of U.S. patent application Ser. No. 12/673,916, which claims the benefit of International Patent Application No. PCT/IN2009/000299, filed May 25, 2009, which in turn claims priority to Indian Patent Application No. 1284/CHE/2008, filed May 26, 2008, the entire disclosures which are incorporated herein by reference.

FIELD OF THE INVENTION

The present invention relates to improved processes for the preparation of Montelukast and its salts thereof.

BACKGROUND OF THE INVENTION

Montelukast sodium namely Sodium 1-[[[(1R)-1-[3-[(1E)-2-(7-chloro-2-quinolinyl)ethenyl]phenyl]-3-[2-(1-hydroxy-1-methylethyl)phenyl]propyl]thio]methyl]cyclo propane acetic acid has the formula

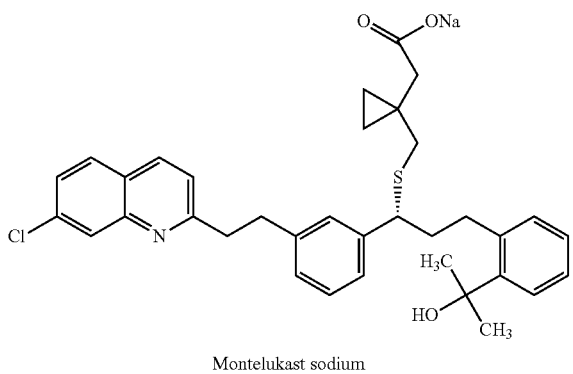

Montelukast sodium

Montelukast sodium is a leukotriene antagonist and inhibits the synthesis of leukotriene biosynthesis. It is useful as anti-asthmatic, anti-allergic, anti-inflammatory, cytoprotective agent and hence useful in the treatment of angina, cerebral spasm, glomerular nephritis, hepatic, end LS toxemia, uveitis and allograft rejection.

EP 0 480 717 discloses Montelukast sodium along with other related compounds and the methods for their preparation. The reported method of synthesis proceeds through corresponding methyl ester namely, and involves coupling methyl 1-(mercaptomethyl)cyclopropane acetate with a mesylate generated in-situ. The methyl ester is hydrolyzed to free acids and the latter to converted directly to Montelukast sodium salt. The process is not suitable for large-scale production because it requires tedious chromatographic purification of the methyl ester intermediate and for the final product with low yield.

U.S. Pat. No. 5,614,632 discloses a process for the preparation of the sodium salt of montelukast and certain process intermediates. The process involves generation of dilithium dianion of 1-(mercaptomethyl)cyclopropaneacetic acid followed by condensation with 2-(2-(3(S)-(3-(2-(7-chloro-2-quinolinyl)ethenyl)phenyl)-3-methanesulfonyloxypropyl) phenyl)-2-propanol (referred as mesylated alcohol) to afford montelukast, which is further converted to the corresponding sodium salt via dicyclohexyl amine salt. The '362 patent also discloses a process for the preparation of crystalline montelukast sodium salt and mesylated alcohol. The process involves reacting methyl 2(3(S)-(3-(2-(7-chloro-2-quinolinyl)ethenyl)phenyl)-3-hydroxy propyl)benzoate with methyl magnesium chloride to give a diol, which is further converted to mesylated alcohol on reaction with methane sulfonyl chloride. While certain processes of its preparation are known, there is a continuing need for new processes of preparation of montelukast and its salts. It is mentioned by the inventors of U.S. Pat. No. 5,614,632, that the crystalline montelukast dicyclohexylamine salt offers an efficient method for the purification of montelukast, which circumvents the need to use chromatographic purification.

Processes for preparation of montelukast and its intermediates have also been described in U.S. Pat. No. 5,523,477, and U.S. Patent Application Publication Nos. 2005/0234241, 2005/0256156, 2005/0107612, and International Application Publication Nos. WO 2005/105749, WO 2005/000807, WO 2004/108679, and WO 2006/021974.

WO 2006/08751 discloses a process for preparation of Montelukast sodium by neutralizing Montelukast organic amine salts such as [alpha]-Methyl benzyl amine salt, diisopropyl amine salt, dibenzyl amine salt followed by treatment with ethanolic sodium hydroxide.

Although many processes have been described in the prior art for the preparation of montelukast and its intermediates, there still remains a need for a process for the preparation of montelukast which is industrially viable.

SUMMARY OF THE INVENTION

The main object of the present invention is to provide an improved process for the preparation of Montelukast and its salts thereof.

Another object of the present invention is to provide novel amine salts of Montelukast.

Another object of the invention is to provide a process for the preparation of novel amine salts of Montelukast.

Another object of the present invention is to provide a process for the preparation of Montelukast alkali/alkaline salts using amine salts of Montelukast.

Another object of the present invention is to provide a process for the preparation of Montelukast alkali/alkaline salts without isolating Montelukast free acid.

Another object of the present invention is to provide a process for the preparation of Montelukast and its salts which is scalable and economical.

The present invention is best described with the following synthetic scheme-1;

Scheme-1

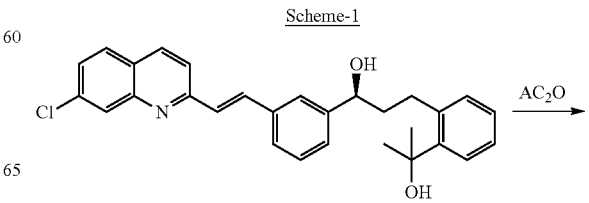

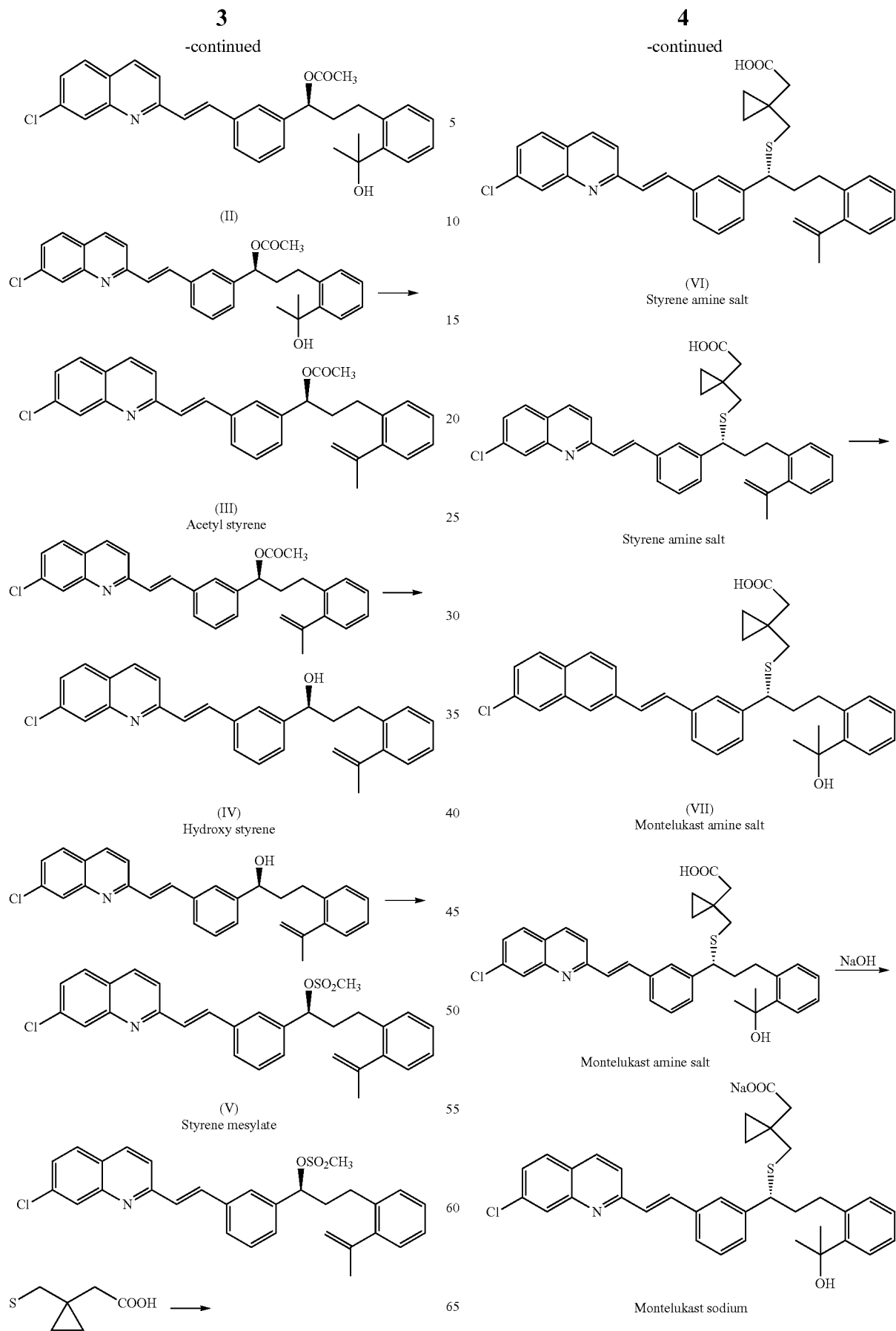

DETAILED DESCRIPTION OF THE INVENTION

In accordance with the present invention the main object is to prepare montelukast and salts thereof comprising the steps of;
a. Treating 2-[2-[3(S)-[3-[2-(7-Chloro-2-quniolinyl)ethenyl]phenyl]-3-hydroxypropyl]phenyl]-2-propanol with acetic anhydride followed by dehydration with PTSA yields (S)-1-(3-((E)-2-(7-chloroquinolin-2-yl)vinyl)phenyl)-3-(2-isopropenylphenyl]propyl acetate of formula (III)
b. Converting (S)-1-(3-((E)-2-(7-chloroquinolin-2-yl)vinyl)phenyl)-3-(2-isopropenylphenyl]propyl acetate to (S)-1-(3-((E)-2-(7-chloroquinolin-2-yl)vinyl)phenyl)-3-(2-isopropenylphenyl]propan-1-ol of formula (IV) (hydroxy styrene)
c. Treating (S)-1-(3-((E)-2-(7-chloroquinolin-2-yl)vinyl)phenyl)-3-(2-isopropenylphenyl]propan-1-ol with mesyl chloride or tosyl chloride yields (S)-1-(3-((E)-2-(7-chloroquinolin-2-yl)vinyl)phenyl)-3-(2-isopropenylphenyl]propyl methane sulphonate or tosylate of formula (V) (mesylated or tosylated styrene)
d. Condensing (S)-1-(3-((E)-2-(7-chloroquinolin-2-yl) vinyl) phenyl)-3-(2-isopropenylphenyl]propyl methane sulphonate or tosylate with 1-(mercapto methyl)cyclopropane acetic acid followed by saltification with an amine gives (1-[(R)-1-(3-[(E)-2-(7-chloroquinolin-2-yl)vinyl]-phenyl)-3-(2-isopropenylphenyl)propylsulfanylmethyl]cyclopropyl]acetic acid amine salt (styrene amine salt) of formula (VI).
e. Converting (1-[(R)-1-(3-[(E)-2-(7-chloroquinolin-2-yl) vinyl]-phenyl)-3-(2-isopropenylphenyl)propylsulfanylmethyl]cyclopropyl]acetic acid amine salt to montelukast amine salt of formula (VII)
f. Converting Montelukast amine salt to Montelukast free acid and or its required alkali/alkaline salt In a preferred embodiment, 2-[2-[3(S)-[3-[2-(7-Chloro-2-quniolinyl)ethenyl]phenyl]-3-hydroxypropyl]phenyl]-2-propanol is treated with acetic anhydride followed by dehydration with PTSA yields (S)-1-(3-((E)-2-(7-chloroquinolin-2-yl)vinyl)phenyl)-3-(2-isopropenylphenyl]propylacetate of Formula (III). The compound of formula (III) is converted to (S)-1-(3-((E)-2-(7-chloroquinolin-2-yl)vinyl)phenyl)-3-(2-isopropenylphenyl]propan-1-ol (hydroxy styrene) of Formula (IV)

The compound of formula (IV) is mesylated with methane sulfonyl chloride or tosylated with toluene sulfonyl chloride to form (S)-1-(3-((E)-2-(7-chloroquinolin-2-yl)vinyl)phenyl)-3-(2-isopropenylphenyl]propyl methane sulphonate (mesylated styrene) of formula (V) or a corresponding tosylate. Also, use of other leaving group-containing compounds instead of the mesylate or tosylate intermediate is also contemplated. The reaction may process in polar solvent or non-polar solvent, or in a mixture of polar and non-polar organic solvents. The resulting leaving group containing intermediate (e.g., mesylate or tosylate, preferably, mesylate is then condensed with 1-mercapto methyl cyclopropane acetic acid of formula in the presence of a base. The use of a mixture of polar organic solvents is preferred. The product of this reaction is preferably isolated in the form of an organic amine salt, preferably, dicyclohexyl amine salt of formula (VI).

The resultant amine salt is reacted with sulphuric acid to get Montelukast free acid and is again converted to its organic amine salt of formula (VII) to get more pure compound. The amine salt of Montelukast of formula (VII) is conveniently converted into alkali/alkaline salts, preferably sodium salt using sodium methoxide or sodium hydroxide.

In a specific embodiment, the invention provides a process for the preparation of Montelukast and its pharmaceutically acceptable salts, preferably, its sodium salt, which involves:
a) reacting the hydroxy styrene compound with methane sulfonyl chloride in the presence of a tertiary amine, for example, diisopropyl ethyl amine or triethyl amine, in a polar and non-polar or mixture of organic solvents at a temperature of −25 to 50° C.;
b) stirring the reaction mass obtained in step (a) till the reaction substantially completes and subsequently working up the mixture to obtain the mesylated compound of formula (V);
c) reacting the mesylated compound of formula (V) with 1-mercapto methyl cyclopropane acetic acid in polar organic solvents or mixture of polar solvents in the presence of a base, for example, sodium methoxide, sodium ethoxide, sodium hydride, n-butyl lithium, or cesium carbonate preferably 25% sodium methoxide in methanol at a temperature of −15 to 60° C.;
d) stirring the reaction mass obtained in step (c) till the reaction complies and subsequently working it up to obtain a styrene compound, which is then reacted with dicyclohexyl amine salt to afford the amine salt of formula (VI);
e) treating the dicyclohexyl amine salt of formula (VI) with sulphuric acid wherein the sulphuric acid is either aqueous or concentrated at a temperature of −20 to +50° C.;
f) stirring the reaction mass obtained in step (e) till the reaction complies and subsequently working it up to isolate Montelukast acid and further reacting the resultant montelukast free acid with primary, secondary or tertiary amines, preferably 1-methyl-3-phenylpropylamine, 1,2-cyclohexyl diamine to afford the amine salt of formula (VII);
g) converting the amine salt into its pharmaceutically acceptable salts by generating the montelukast free acid from montelukast amine salt in halogenated solvents, for example, chloroform, dichloromethane or dichloroethane, preferably, dichloromethane, or an aromatic hydrocarbon, for example toluene in the presence of an organic acid, preferably acetic acid;
h) converting the obtained solution in step (g) to sodium salt of Montelukast using sodium hydroxide, sodium methoxide or sodium ethoxide in alcohols such as from methanol, ethanol, propanol, butanol, 2-propanol or tert.butanol, preferably, by using ethanolic sodium hydroxide;
i) distilling the solvent from the reaction solution of step (g) under reduced pressure and;
j) dissolving the above residue in methanol and treating with activated carbon
k) distilling methanol completely and isolating the desired product by adding cyclohexane, n-pentane, n-heptane or hexanes; and
l) drying the isolated solid at 50-95° C. under vacuum.

The Montelukast sodium obtained in the present novel process is having >99.0% enantiomeric excess purity and resulted in amorphous form. The Montelukast sodium obtained in the present process is also free flowing and non-solvated solid; hence it is well suited for pharmaceutical applications.

Unless stated to the contrary, any use of the words such as "including," "containing," "comprising," "having" and the like, means "including without limitation" and shall not be construed to limit any general statement that it follows to the specific or similar items or matters immediately following it. Except where the context indicates to the contrary, all exemplary values are intended to be fictitious, unrelated to actual entities and are used for purposes of illustration only. Most of the foregoing alternative embodiments are not mutually exclusive, but may be implemented in various combinations. As these and other variations and combinations of the features discussed above can be utilized without departing from the invention as defined by the claims, the foregoing description of the embodiments should be taken by way of illustration rather than by way of limitation of the invention as defined by the appended claims.

EXAMPLES

The present invention will now be further explained in the following examples. However, the present invention should not be construed as limited thereby. One of ordinary skill in the art will understand how to vary the exemplified preparations to obtain the desired results.

Example-I

Preparation of (S)-1-(3-((E)-2-(7-chloroquinolin-2-yl)vinyl)phenyl)-3-(2-(1-hydroxy-1-methylethyl) phenyl]propyl acetate To a stirred solution of 2-[2-[3(S)-[3-[2-(7-Chloro-2-quniolinyl)ethenyl]phenyl]-3-hydroxypropyl]phenyl]-2-propanol (100 gm) in dichloromethane (500 ml) at 25-30° C. 4-di(methyl amino)pyridine (5.32 gm) was added and cooled to 0° C. To the reaction mixture Triethylamine (26.4 gm) was added at 0° C. Acetic anhydride (26.7 gm) was added slowly at temp. 0-5° C. over 30-60 min and maintained the reaction at temp. 0-5° C. over 30 min. Reaction completion was monitored by TLC. After reaction completion the reaction mass was quenched into 7% NaHCO₃ (500 ml) and stirred for 15 min. Temperature was raised to 25-30° C. and maintained for 30 min. Reaction mass was settled for 15 min and separated the organic layer. Aq. layer was extracted with dichloromethane (250 ml). The combined organic layer was washed with 25% NH₄Cl solution (500 ml). Organic layer was distilled below 40° C. to get the desired product as residue.
Output: 108.0 gm

Example-II

Preparation of (S)-1-(3-((E)-2-(7-chloroquinolin-2-yl)vinyl)phenyl)-3-(2-isopropenylphenyl]propyl acetate PTSA (62.4 gm) was suspended in toluene (300 ml) at 25-30° C. and moisture was removed by azeotropic distillation. After removal of moisture reaction mass was cooled to 70° C. and distilled toluene completely under reduced pressure to get residue. The obtained residue was cooled to room temperature and charged dichloromethane (300 ml) and stage-I (108 gm of stage-I dissolved in 200 ml dichloromethane). The reaction mass temp was raised to reflux and maintained for 2 hrs. Reaction completion was monitored by TLC. After reaction completion the reaction mass was quenched into 7% NaHCO₃ (300 ml) and stirred for 15 min. Reaction mass temp was raised to 25-30° C. and maintained for 30 min. Reaction mass was settled for 15 min and the organic layer was separated. Aq. layer was extracted with dichloromethane (200 ml) at 25-30° C. The combined organic layer was washed with of DM Water (2×300 ml). Organic layer was concentrated below 40° C. to get the desired product as residue.
Output: 101.2 gm

Example-III

Preparation of (S)-1-(3-((E)-2-(7-chloroquinolin-2-yl)vinyl)phenyl)-3-(2-isopropenylphenyl]propan-1-ol HCl To a stirred solution of Stage-II (101 gm) in methanol (500 ml) NaOH solution (35 gm of NaOH dissolved in 52 ml DM Water) was added at 25-30° C. over 30 min. Reaction completion was checked by TLC. After reaction completion methanol and water were completely distilled under reduced pressure below 50° C. The residue was dissolved in ethyl acetate (600 ml). To the obtained solution DM water (500 ml) was added pH was adjusted to 6.5-7.0 slowly with 1:1 dil HCl at 25-30° C. Aq layer was separated and again extracted with ethyl acetate (200 ml). The combined organic layer was washed with DM Water (500 ml). The separated organic layer was dried over sodium sulphate and concentrated completely under reduced pressure at temp below 45° C. The obtained residue was dissolved in methanol (300 ml) and methanolic HCl (80 ml of 8%) was added over 30-60 min at room temperature. Reaction mixture was maintained for 2 hrs at room temperature one hour at 10-15° C. The precipitated product was filtered and washed the wet cake with chilled methanol (50 ml).
Output: 88.0 gm

Example-IV

Preparation of (S)-1-(3-((E)-2-(7-chloroquinolin-2-yl)vinyl)phenyl)-3-(2-isopropenylphenyl]propyl methane sulphonate To a stirred solution of compound obtained in Example-III (100 gm) in dichloromethane (600 ml), DM water (300 ml) was charged and pH was adjusted to 7.5 to 8.0 with ammonia solution at 25-30° C. Reaction mass was stirred for 30 min at 25-30° C. and settled for 10 min. Organic layer was separated and the aq. layer was extracted with dichloromethane (200 ml). The combined organic layer was washed with DM Water (2×300 ml). Dichloromethane was distilled completely below 40° C. to get residue. The obtained residue was dissolved in dichloromethane (600 ml) and cooled to 0° C. Di isopropyl ethyl amine (DIPEA) (40.6 gm) was added under N₂ atmosphere and again cooled to −30° C. Methane sulphonyl chloride (31.33 gm) was added at −30 to −25° C. slowly over 60 min and maintained the reaction at −30° to −25° C. for 2 hrs under N₂ atmosphere. Reaction completion was checked by TLC. After reaction completion, the reaction mass was quenched in to 7% NaHCO₃ (1000 ml) below 5° C. The reaction mass was maintained for 10 min at 0-5° C. and 30 min at 25-30° C. Organic layer was separated and aq. layer was extracted with dichloromethane (200 ml). The combined organic layer was washed with DM water (2×500 ml). Dichloromethane was distilled out completely below 40° C. to get desired product as residue.
Output: 105.0 gm

Example-V

Preparation of (S)-1-(3-((E)-2-(7-chloroquinolin-2-yl) vinyl) phenyl)-3-(2-isopropenylphenyl]propyl methane sulphonate To a stirred solution of Stage-III (100 gm) in dichloromethane (300 ml) Diisopropylethylamine (27.1 gm) was charged and Reaction mass was stirred for 30 min at 40-45° C.

Dichloromethane was distilled completely below 40° C. to get residue. The obtained residue was dissolved in dichloromethane (1000 ml) and cooled to 0° C. Di isopropyl ethyl amine (DIPEA) (40.6 gm) was added under $N_2$ atmosphere and again cooled to 0° C. Methane sulphonyl chloride (31.33 gm) was added at 0 to 5° C. slowly over 60 min and maintained the reaction at 0° to 5° C. for 2 hrs under $N_2$ atmosphere. Reaction completion was checked by TLC. After reaction completion, the reaction mass was quenched in to 7% $NaHCO_3$ (1000 ml) below 5° C. The reaction mass was maintained for 10 min at 0-5° C. and 30 min at 25-30° C. Organic layer was separated and aq. layer was extracted with dichloromethane (200 ml). The combined organic layer was washed with DM water (2×500 ml). Dichloromethane was distilled out completely below 40° C. to get desired product as residue.

Output: 105.0 gm

Example-VI

Preparation of DCHA salt of (1-[(R)-1-(3-[(E)-2-(7-chloroquinolin-2-yl)vinyl]-phenyl)-3-(2-isopropenylphenyl)propylsulfanylmethyl]cyclopropyl]acetic acid (Styrene DCHA salt)

To a stirred solution of 1-(mercapto methyl)cyclopropane acetic acid (46 gm) in DMF (300 ml), NaH (25 gm) was added in four equal lots over 60 min at –5-0° C. The reaction mixture was maintained for 2 hrs at –5-0° C. Stage-IV (100 gm dissolves in 300 ml of DMF) was added at –5-0° C. over 1 hr. The reaction mixture was maintained at 0-5° C. for 15 hrs. The reaction completion was checked by TLC. After reaction completion reaction mixture was quenched in to mixture of 10% NaCl (1000 ml), and ethyl acetate (1000 ml) below 10° C. Reaction mixture was stirred for 10 min at 0-10° C. and 30 min at room temperature. Organic layer was separated and the aq. layer was extracted with ethyl acetate (500 ml). The combined organic layer, was washed with 5% tartaric acid solution (500 ml) followed by of DM. Water (2×500 ml). Separated organic layer was dried over 25 g of Sodium sulphate. Ethyl acetate was distilled completely under reduced pressure below 45° C. The obtained residue was dissolved in ethyl acetate (600 ml) at room temperature. To the above solution dicyclohexyl amine (50 ml) was added at room temperature over 30 min under nitrogen atmosphere. Reaction mixture was maintained for 1 hr at room temperature and seeded with pure dicyclohexyl amine salt. Reaction mixture was maintained for 12-24 hrs at room temperature. n-Hexane (1200 ml) was added slowly at room temperature over 60 min and maintained for 12 hrs. The precipitated product is filtered and washed with of n-Hexane (200 ml).

Output: 100.0 gm

Example-VII

Preparation of DCHA salt of (1-[(R)-1-(3-[(E)-2-(7-chloroquinolin-2-yl)vinyl]-phenyl)-3-(2-isopropenylphenyl)propylsulfanylmethyl]cyclopropyl]acetic acid (Styrene DCHA salt)

To a stirred solution of 1-(mercapto methyl)cyclopropane acetic add (36.7 gm) in DMF (300 ml), sodium methoxide (108.6 gm 25% methanolic soln) was added over 60 min at 0-5° C. The reaction mixture was maintained for 2 hrs at 0-5° C. mesylated Styrene (100 gm dissolves in 300 ml of DMF) was added at 0-5° C. over 1 hr. The reaction mixture was maintained at 0-5° C. for 15 hrs. The reaction completion was checked by TLC. After reaction completion reaction mixture was quenched in to mixture of 10% NaCl (1000 ml), and ethyl acetate (1000 ml) below 10° C. Reaction mixture was stirred for 10 min at 0-10° C. and 30 min at room temperature. Organic layer was separated and the aq. layer was extracted with ethyl acetate (500 ml). The combined organic layer was washed with 5% tartaric acid solution (500 ml) followed by of DM Water (2×500 ml). Separated organic layer was dried over 25 g of Sodium sulphate. Ethyl acetate was distilled completely under reduced pressure below 45° C. The obtained residue was dissolved in ethyl acetate (600 ml) at room temperature. To the above solution dicyclohexyl amine (50 ml) was added at room temperature over 30 min under nitrogen atmosphere. Reaction mixture was maintained for 1 hr at room temperature and seeded with pure dicyclohexyl amine salt. Reaction mixture was maintained for 12-24 hrs at room temperature. n-Hexane (1200 ml) was added slowly at room temperature over 60 min and maintained for 12 hrs. The precipitated product is filtered and washed with of n-Hexane (200 ml).

Output: 101.0 gm

Example-VIII

Preparation of Montelukast Amine Salt

To a stirred solution of Styrene DCHA salt (100 gm) in dichloromethane (500 ml) to DM Water (300 ml) was charged and pH was adjusted 4.0 to 4.5 with 1:1 dil Acetic acid at 25-30° C. The reaction mixture was stirred for stirred for 30 min at room temperature. Organic layer was separated and aq. layer was extracted with dichloromethane (300 ml). The combined organic layer was washed with DM water (2×300 ml). Organic layer was concentrated under below 40° C. to get semi solid material. n-Hexane (500 ml) was added and stirred for 30 min at room temperature. The precipitate was filtered and washed the wet cake with n-Hexane (100 ml). The wet product was dried at 40-45° C. to get styrene free acid (73 gm).

Styrene free acid (73 gm) was added to sulfuric acid (365 ml of 80%) in equal lots at 5°-10° C. Reaction mass was maintained for 1 hr. at 5-10° C. Reaction completion was monitored by TLC. After the reaction completion (product is ~65%; styrene is ~30%) the reaction mass was quenched into a mixture of DM water (730 ml), ethyl acetate (730 ml) and t-butanol (730 ml) below 10° C. After quenching the reaction mass pH was adjusted to 3.5-4.0 with 20% NaOH below 10° C. Again the temperature was raised to 25-30° C. and maintained for 30 min. Organic layer was separated and aq. layer was extracted with ethyl acetate (2×730 ml) at room temperature. The combined organic layer was washed with DM water (2×730 ml). The organic layer was over sodium sulphate and concentrated under reduced pressure below 45° C. to get the desired product as residue. The obtained residue was subjected to column chromatography (Mobile phase is dichloromethane:methanol, 99.5:0.5). The separated montelukast free acid was dissolved in ethyl acetate (180 ml) at 40° C. and cooled to room temperature under $N_2$ atmosphere.

To the obtained solution 1-methyl-3-phenylpropylamine (9.7 ml) was added slowly at 25-30° C. over 30 min. Reaction mass was maintained for 60 min, seeded and maintain for 12-16 hrs at 25-30° C. under $N_2$ atmosphere. After the product was precipitated, n-Hexane (360 ml) was added slowly over 1 hr at 25-30° C. The reaction mass was maintained at 25-30° C. for 12 hrs. The precipitated product was filtered and washed the wet cake with n-Hexane (60 ml). The wet product was dried at 45-50° C. The dried product was purified by recrystallization in toluene.

Output: 70.0 gm

Example-IX

Preparation of Montelukast Amine Salt

To sulfuric acid (500 ml of 80%) styrene DCHA salt (100 gm) was added in equal lots at 5°-10° C. Reaction mass was maintained for 1 hr at 5-10° C. Reaction completion was monitored by HPLC. After the reaction completion the reaction mass was quenched into a mixture of DM water (1000 ml), ethyl acetate (1000 ml) and t-butanol (1000 ml) below 10° C. After quenching the reaction mass pH was adjusted to 3.5-4.0 with 20% NaOH below 10° C. Again the temperature was raised to 25-30° C. and maintained for 30 min. Organic layer was separated and aq. layer was extracted with ethyl acetate (2×500 ml) at room temperature. The combined organic layer was washed with 5% brine (2×1000 ml). The organic layer was over sodium sulphate and concentrated under reduced pressure below 45° C. to get the desired product as residue. The obtained residue was subjected to column chromatography (Mobile phase is dichloromethane:methanol, 99.5:0.5). The separated montelukast free acid was dissolved in ethyl acetate (300 ml) at 40° C. and cooled to room temperature under $N_2$ atmosphere.

To the obtained solution 1-methyl-3-phenylpropylamine (16.2 ml) was added slowly at 25-30° C. over 30 min. Reaction mass was maintained for 60 min, seeded and maintain for 12-16 hrs at 25-30° C. under $N_2$ atmosphere. After the product was precipitated, n-Hexane (600 ml) was added slowly over 1 hr at 25-30° C. The reaction mass was maintained at 25-30° C. for 12 hrs. The precipitated product was filtered and washed the wet cake with n-Hexane (100 ml). The wet product was dried at 45-50° C. The dried product was purified by recrystallization in toluene.

Output: 50.0 gm
Purity by HPLC: 98.2%

Example-X

Preparation of Montelukast Sodium Salt

To a suspension of Montelukast 1-methyl-3-phenylpropylamine salt (100 gm) in dichloromethane (2000 ml) DM water (1000 ml) was charged pH was adjusted to 4.0 to 4.5 with acetic acid (1:1) at 25-30° C. Reaction mass was maintained at 25-30° C. for 30 min and settle for 20 min. Organic layer was separated and aq. layer was extracted with dichloromethane (1000 ml). The combined organic layer was washed with DM Water (1000 ml). To the organic layer ethanolic NaOH solution (235 ml of ethanol, 2.1 ml of DM Water and 5.17 g of NaOH) was slowly added over 30 min and maintained at 25-30° C. for 30 min. Dichloromethane was distilled completely below 40° C. to get semi solid material. Then methanol (800 ml) was charged at 40-45° C. under $N_2$ atmosphere and stirred for 10 min. The obtained clear solution was treated with activated carbon and filtered the mass over hyflo bed and washed with methanol (200 ml). The clear filtrate was distilled out completely under reduced pressure below 45° C. Pentane (100 ml) was charged to the above residue and distilled out methanol traces completely below 45° C. Again Pentane (2000 ml) was and maintained for 4 hrs at 25-30° C. under $N_2$ atmosphere. The precipitated product was filtered under $N_2$ atmosphere and washed the wet cake with Pentane (100 ml). The obtained wet cake was dried under vacuum for 2 hrs at 50° C., 2 hr at 70-75° C. finally at 85-95° C. for 24 hrs.

Output: 70.0 gm
HPLC Purity: 99.5%

We claim:

1. A process for preparation of Montelukast or a salt thereof, said process comprising the steps of:
   condensing styrene mesylate of formula (V)

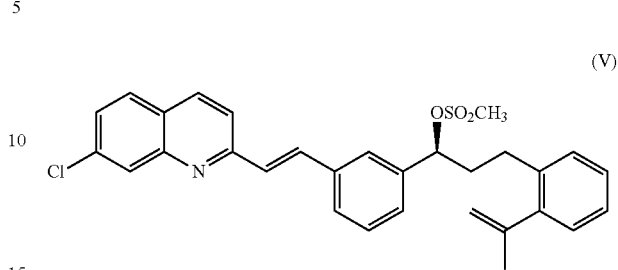

(V)

with 1-(mercaptomethyl)cyclopropane acetic acid with an amine to obtain (1-[(R)-1-(3-[(E)-2-(7-chloroquinolin-2-yl)vinyl]-phenyl)-3-(2-isopropenylphenyl)propylsulfanylmethyl]cyclopropyl]acetic acid styrene amine salt;
   converting the styrene amine salt to Montelukast amine salt; and
   converting the Montelukast amine salt to Montelukast free acid or an alkali or alkaline salt of Montelukast.

2. The process of claim 1, wherein the condensing step is carried out in a polar solvent in the presence of a base.

3. The process of claim 2, wherein said polar solvent is selected from the group consisting of N,N-dimethylformamide, dimethylsulphoxide, N,N-dimethylacetamide, N-methylpyrrolidine, methanol, THF and mixtures thereof.

4. The process of claim 2, wherein said base is selected from the group consisting of metal alkoxides, metal hydrides, metal carbonates, alkyl lithium salts and mixtures thereof.

5. The process of claim 1, wherein the styrene amine salt is dicyclohexylamine salt.

6. The process of claim 1, wherein the first converting step comprises the steps of:
   treating said styrene amine salt with sulphuric acid; and
   isolating the obtained Montelukast as an amine salt.

7. The process of claim 1, wherein the first converting step comprises the steps of:
   converting said styrene amine salt to its free acid;
   treating said free acid with sulphuric acid; and
   isolating the obtained Montelukast as an amine salt.

8. The process of claim 1, wherein said Montelukast amine salt is selected from the group consisting of 1-methyl-3-phenylpropylamine, 1,2-cyclohexyl diamine salt and mixtures thereof.

9. The process of claim 1, wherein the second converting step comprises the steps of:
   converting said Montelukast amine salt to its free acid;
   treating the free acid with an alkali or alkaline base; and
   isolating the resultant alkali or alkaline salt of Montelukast.

10. The process of claim 1, wherein the second converting step comprises the steps of:
    providing a solution of Montelukast free acid in one of a halogenated solvent, aromatic solvent, alkanols and mixtures thereof;
    treating said solution with an alcoholic base to convert said Montelukast free acid to an alkali or an alkaline salt of Montelukast;
    concentrating the reaction mass by drying; and
    adding a cyclic or acyclic hydrocarbon solvent to said solution thereby precipitating said alkali or alkaline salt of Montelukast.

11. The process of claim 1, wherein the second converting step comprises the steps of:
   treating said Montelukast amine salt with an alkali or an alkaline base; and isolating Montelukast as its alkali or alkaline salt.

12. The process of claim 1, wherein the second converting step comprises the steps of:
   providing a solution of Montelukast amine salt in one of a halogenated solvent, aromatic solvent, or mixtures thereof;
   treating said solution with an alkali or an alkaline base to convert said Montelukast amine salt into a salt of Montelukast;
   concentrating the reaction mass to dryness; and
   adding a cyclic or acyclic hydrocarbon solvent to said solution to precipitate said alkali or alkaline salt of Montelukast.

13. The process of claim 12, wherein the alkali or alkaline base is selected from the group consisting of sodium hydroxide, sodium methoxide and sodium ethoxide in an alcohol; and wherein the alcohol is selected from the group consisting of methanol, ethanol, propanol, butanol, 2-propanol and tert-butanol.

14. The process of claim 10, wherein said hydrocarbon solvent is selected from the group consisting of cyclohexane, pentane, hexane, heptane and mixtures thereof.

15. The process of claim 12, wherein said hydrocarbon solvent is selected from the group consisting of cyclohexane, pentane, hexane, heptane and mixtures thereof.

16. The process of claim 1, wherein the condensing step is performed at a temperature of −15° C. to 60° C.

17. The process of claim 1, wherein the first converting step is performed at a temperature of −20° C. to 50° C.

18. The process of claim 10, wherein the halogenated solvent is selected from the group consisting of chloroform, dichloromethane, and dichloroethane.

19. The process of claim 10, wherein the aromatic solvent is toluene.

20. A method for making 1-methyl-3-phenylpropylamine salt of Montelukast comprising the steps of
   condensing styrene mesylate of formula (V)

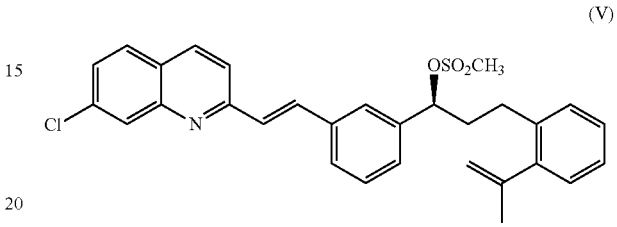

(V)

with 1-(mercaptomethyl)cyclopropane acetic acid and 1-methyl-3-phenylpropylamine to obtain (1-[(R)-1-(3-[(E)-2-(7-chloroquinolin-2-yl)vinyl]-phenyl)-3-(2-isopropenylphenyl) propylsulfanylmethyl]cyclopropyl]acetic acid styrene 1-methyl-3-phenylpropylamine salt;
   treating the styrene 1-methyl-3-phenylpropylamine salt with sulfuric acid to produce Montelukast 1-methyl-3-phenylpropylamine salt.

* * * * *